United States Patent [19]

Simpson et al.

[11] Patent Number: 5,292,946
[45] Date of Patent: Mar. 8, 1994

[54] IN-SITU PREPARATION OF DIISOPINOCAMPHENYL CHLOROBORANE

[75] Inventors: Pamela M. Simpson, North Brunswick; David M. Tschaen, Aberdeen; Thomas R. Verhoeven, Watchung, all of N.J.

[73] Assignee: Merck & Co., Inc., Rahway, N.J.

[21] Appl. No.: 859,595

[22] Filed: Mar. 23, 1992

Related U.S. Application Data

[63] Continuation of Ser. No. 586,933, Sep. 24, 1990, abandoned.

[51] Int. Cl.⁵ .............................................. C07F 5/02
[52] U.S. Cl. ...................................... 562/806; 560/51; 560/60
[58] Field of Search ................ 562/806; 560/51, 60

[56] References Cited

PUBLICATIONS

J. Org. Chem. 1984, 49, 945–947.
Chemical Abstracts 104(9):69021r, 1985.

*Primary Examiner*—Paul J. Killos
*Attorney, Agent, or Firm*—Curtis C. Panzer; David L. Rose; Joseph F. DiPrima

[57] ABSTRACT

The present invention is directed to in-situ preparation of diisopinocamphenylchloroborane, and the use of same in the reduction of prochiral ketones to optically active alcohols such as those of formula B.

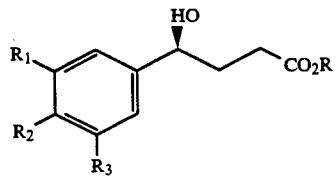

The compound of Formula B is useful in the production 2,5-diaryltetrahydrofurans useful as PAF antagonists.

4 Claims, No Drawings

IN-SITU PREPARATION OF DIISOPINOCAMPHENYL CHLOROBORANE

This is a continuation of application Ser. No. 07/586,933, filed Sep. 24, 1990 abandoned.

BACKGROUND OF THE INVENTION

The invention concerns the preparation of diisopinocampheylborane. The invention also relates to the use of a crude diisopinocampheyl borane product in the reduction of prochiral ketones.

Previously, diisopinocampheylborane was prepared and isolated by crystallization prior to its conversion to the active reducing agent diisopinocampheylchloroborane. This intermediate is highly sensitive to both oxygen and water, thus complicating its isolation.

Isolation by crystallization had the effect of increasing the enantiomeric purity of the reagent to >99%, starting from pinene of an optical purity of approximately 90%. This upgrading of the enantiomeric purity of the reducing reagent via crystallization was deemed critical for obtaining maximum enantioselectivity in the reduction of ketones to alcohols. See Brown, H. C.; Park, W. S.; Cho, B. T.; Ramachandran, P. V. *J. Org. Chem.*, 1987, 52, 5406 and references therein; Brown, H. C.; Chandrasekharan, J.; Ramachandran, J.; Ramachandran, P. V. *J. Org. Chem.* 1986, 51, 3394; Srebnik, M. Ramachandran, P. V.; Brown, H. C. *J. Org. Chem.*, 1988, 53, 2916; and Brown, H. C.; Chandrasekharan, J.; Ramachandran, P. V. *J. Am. Chem. Soc.* 1988, 1539.

The present invention demonstrates this previously held tenet to be false. Diisopinocampheylborane is prepared in-situ, without isolation or discrete purification, and yet surprisingly performs in an equal manner to isolated reagent. This represents a major process advantage since both the diisopinocampheylborane and the diisopinocampheylchloroborane are highly reactive reagents, sensitive to both oxygen and water. Thus handling of these reagents, which would be necessitated during isolation, presents difficulty.

The present invention also concerns the use of a crude diisopinocampheylborane product in the preparation of the chiral alcohols such as those of the intermediate compounds of Formula B.

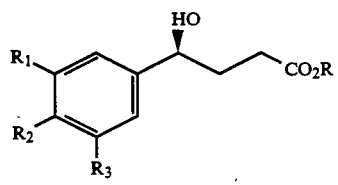

B

Use of diisopinocampheyl chloroborane in the preparation of the chiral alcohols is described in the references cited above. Use of diisopinocampheyl chloroborane in the preparation of the chiral hydroxides of Formula B is described in co-pending applications U.S. Ser. Nos. 546,486 abandoned and 546,486 filed by Shinkai et al., Jun. 29, 1990 U.S. Pat. 509,9033. Intermediate compounds of Formula B are useful in making PAF antagonists of Formula I

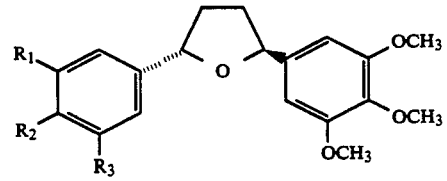

Platelet-activating factor (PAF) has recently been identified as an acetyl glyceryl ether phosphorylcholine (AGEPC), i.e., 1-0-hexadecyl/octadecyl-2acetyl-sn-glyceryl-3-phosphocholione (Hanahan D. J., etal., *J. Biol. Chem.* 255:5514, 1980). PAF has been linked to various biological activities and pathways making it one of the important mediators responsible for a variety of physiological processes including activation or coagulation of platelets, pathogenesis of immune complex deposition, smooth muscle contraction, inflammation, hypotension, shock, pain, edema as well as respiratory, cardiovascular and intravascular alterations. These physiological processes are in turn associated with a large group of diseases, for example, inflammatory disease, cardiovascular disorder, hypotension, shock, psoriasis, allergic and skin diseases, asthma, lung edema, peptic or stomach ulcer, dental pain, and adult respiratory distress syndrome.

Some compounds of formula (I) as well as their utility as PAF antagonists and their method of preparation are disclosed in U.S. Pat. No. 4,539,335 which issued on Sep. 3, 1985; E.P. 0 199 324, which published on Oct. 29, 1986; E.P. 0 322 033, published on Jun. 28, 1989; and co-pending U.S. application Ser. No. 362919, filed Jun. 8, 1989, all of which are incorporated by reference.

U.S. Ser. No. 546,486, filed Jun. 29, 1990, which reference is hereby incorporated by reference discloses a process of making intermediate butyrolactone of Formula D. That process is outlined in Scheme 1.

SCHEME 1

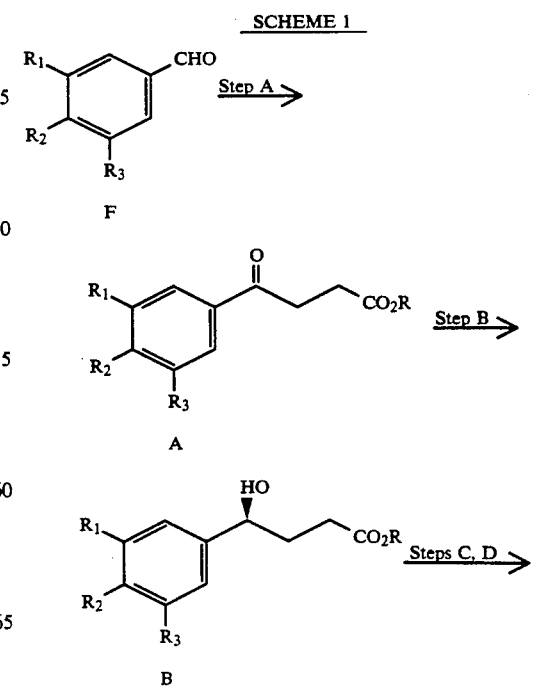

-continued
SCHEME 1

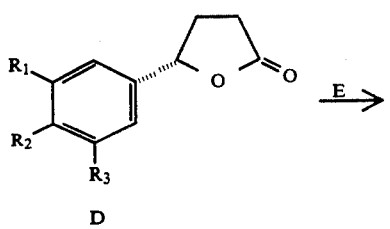

D

In Step A, an in situ prepared acyl anion equivalent, Compound E, which is derived from a substituted benzaldehyde is chemoselectively added to an α,β-unsaturated ester, to yield Compound A. This single transformation assembles the requisite carbon framework from commercially available precursors. In Step B an enantioselective reduction utilizes β-chlorodiisopinocampheyl borane in an unprecedented manner to produce an optically enriched 4-aryl-4-hydroxy-butanoate, Compound B. In Steps C to D conversion of Compound B to the title lactone Compound D is accomplished via a novel, internally assisted saponification followed by a mild acid catalyzed lactonization. Both saponification and lactonization are effected without racemization. Thereafter, controlled crystallization of Compound D efficiently enriches the optical purity to greater than 99.5%.

It is to be noted, however, that U.S. Ser. No. 546,486 utilized a preformed and purified diisopinocampheyl chloroborane.

In sharp contrast the instant process of making a compound of Formula D, comprehends the novel unobvious approach whereby the reactions can be accomplished without the heretofor recognized need to resort to extensive purification.

BRIEF DESCRIPTION OF THE INVENTION

The present invention is directed to in-situ preparation of dissopinocamphenyl chloro borane, and the use of same in the reduction of prochiral ketones to alcohols such as the optically active alcohols of Formula B.

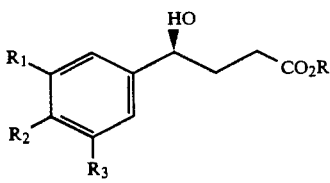

DETAILED DESCRIPTION OF THE INVENTION

The instant invention encompasses a process of making diisopinocampheylchloroborane comprising:

(a) contacting borane methylsulfide in an etheral solvent with (1R)-(+)-α-pinene, to form the diisopininocampheyl borane of Formula 1,

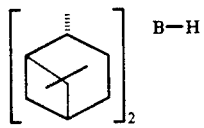

(b) contacting, without further purification, the impure product of step (a) with an acidic chloride to yield diisopininocampheylchloro borane of Formula 2;

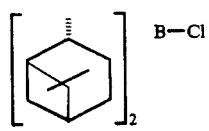

For purposes of this specification the phrase "without further purification" is intended to indicate that the named reaction product (e.g. compound of Formula 1 or 2) is not in any manner or degree isolated from such materials as the solvent, unreacted reagents, or possible side reaction products, that may be present in the reaction vessel. For purposes of this specification the (1R)-(+)-α-pinene shall be understood to have a purity of about 91% ee to 95% ee.

For purposes of this specification and as is understood by those of skill in the art, the etheral solvents include, but are not limited to ethers such as diethyl ether di-n-butyl and diisopentyl ethers, anisole, cyclic ethers such as tetrahydropyran, 4-methyl-1,3-dioxane, dihydropyran, tetrahydrofurfuryl methyl ether, ethyl ether, furan and 2-ethoxytetrahydrofuran, most preferably tetrahydrofuran.

The reaction step (a) can be conducted at −25° to 25° C., preferably at 0° to 5° C. The reaction is allowed to proceed until essentially complete in about 1 to 100 hours, preferably 18 hours. While step (a) may be carried out at up to 100 atmospheres, the reaction is preferably carried out at ambient pressure.

Preferably, the pinene is added to the borane in THF in the absence of oxygen and in a manner calculated to maintain the temperature of the reaction mixture in a range of 0° to 5° C.

The molar ratio of pinene to Borane methyl sulfide should be approximately 2:1. Preferable there should be an excess of pinene, such as 2.1 to 3:1.

For purposes of this specification acid chloride may include, but is not limited to hydrochloric acid. The acid chloride is preferably added in a etheral solvent as described above; preferably the etheral solvent selected for step (a).

As will appreciated by those of skill in the art, the molar amount of acid chloride added should be approximately equal to that of the borane added in step (a).

The reaction step (b) can also be conducted at −25° to 25° C., preferably at 0° to 5° C. The reaction is allowed to proceed until essentially complete in about 0.1 to 1 hours, preferably 15 to 30 minutes. While step (b) may be carried out at up to 100 atmospheres, the reaction is preferably carried out at ambient pressure.

In a second embodiment, the instant invention also encompasses a process for reducing a prochiral ketone to produce an optically active alcohol of high optical purity comprising:

Reacting a prochiral ketone with a reducing agent which is, without further purification the product of step (b) for from 7 hours to 24 days at a temperature from −25° C. to ambient temperature at ambient pressure until the reaction is complete.

This embodiment represents an improvement over U.S. Pat. No. 4,866,181 issued to Brown on Sep. 12, 1989, which is hereby incorporated by reference. In particular this embodiment is useful for carrying out reductions of the following reaction types:

In one class, this latter embodiment encompasses a process for the preparation of 5-aryl-γ-butyrolactones. These compounds are critical intermediates for the synthesis of optically pure trans-2,5-diaryl tetrahydrofurans which are potent antagonists of Platelet Activating Factor.

In particular, the invention concerns a process of making Compounds of Formula B

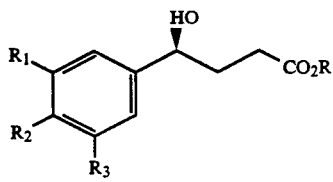

wherein
$R_1$ is iodide; or
$R^1$ is $S(O)_n R_a$ in which n is 0,1 or 2 and $R_a$ is selected from the group consisting of
(a) $C_{1-6}$alkyl,
(b) $C_{1-6}$alkenyl,
(c) $C_{2-6}$alkynyl,
(d) substituted $C_{1-6}$alkyl, wherein the substituent is selected from the group consisting of hydroxy, protected hydroxy, N-$C_{1-4}$alkylamino and N,N-$C_{1-4}$-di-alkylamino
(e) $C_{1-6}$alkoxy-$C_{1-6}$alkyl,
(f) $C_{1-6}$alkylcarbonyl-$C_{1-6}$alkyl; and
$R_2$ is selected from the group consisting of
(a) $C_{1-12}$alkoxy,
(b) $C_{2-6}$alkenyloxy,
(c) $C_{2-6}$alkynyloxy,
(d) $C_{2-6}$(halo)x alkoxy wherein x is 1,2,3,4 or 5 and halo is chloro fluoro or bromo,
(e) substituted $C_{1-8}$alkoxy wherein the substituent is hydroxy or protected hydroxy,
(f) $C_{1-8}$alkoxy-$C_{1-6}$alkoxy,
(g) $C_{1-6}$alkyl $S(O)_m$-$C_{1-6}$alkoxy in which m is 0, 1 or 2,
(h) $C_{1-6}$alkyloxysulfonyl-$C_{1-6}$alkoxy,
(i) $C_{1-6}$alkyl carbonyl-$C_{1-6}$alkoxy,
(j) phenyl-$C_{1-6}$alkoxy,
(k) azido-$C_{1-6}$alkoxy,
(l) cyano-$C_{1-6}$alkoxy,
(m) $C_{1-6}$ alkylS(O)$_m$-$C_{1-6}$alkoxy,
(n) N-substituted or $_{N,N}$ disubstituted amino-$C_{1-6}$ alkoxy, wherein the substituents are each individually $C_{1-6}$alkyl;
$R_3$ is selected from the group consisting of
(a) $C_{1-6}$alkoxy,
(b) substituted $C_{1-6}$alkoxy wherein the substituent is selected from the group consisting of hydroxy, protected hydroxy, N-$C_{1-4}$alkylamino and N,N-$C_{1-4}$ dialkylamino,
(c) —O—$C_{1-6}$alkyl-O—$R^{10}$, wherein $R^{10}$ is
   (1) —PO$_2$(OH)— M+ wherein M+ is a pharmaceutically acceptable cation,
   (2) —C(O)(CH$_2$)$_2$—CO$_2$−M+, or
   (3) —SO$_3$−M+,
(d) $C_{1-6}$-alkylcarbonyl-$C_{1-6}$alkoxy,
(e) $C_{1-6}$-alkoxyaminocarbonyloxy,
(f) halophenyl$C_{1-6}$-alkoxy, and
(g) $C_{1-6}$carboxyalkoxy, comprising:
(A) Contacting, in the substantial absence of oxygen, and in the presence of a catalyst compound of formula F

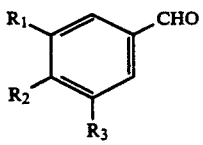

wherein $R_1$ is iodide, with an acrylate derivative of formula $H_2C=C(H)—R$ wherein R is $CO_2Et$, $CO_2Me$, $CO_2CH_2Ph$, $CO_2CH_2CHCH_2$, $CO_2Ph$, $CO_2$—t—$C_4H_9$ or CN, to yield a compound of formula A;

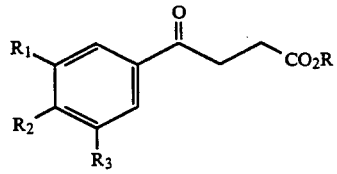

Preferably, contacting Step A is carried out in two stages. The first stage comprises degassing a solution of Compound F in the first solvent, followed by addition of a catalytic amount of alkali metal cyanide to the solution of Compound F in the first solvent. Degassing may conveniently be accomplished by bubbling nitrogen gas through the solution for 10 minutes under ambient conditions. The cyanide is then added and the reagents are stirred for about 10 to 100 minutes. 30 minutes under constant stirring has proven quite satisfactory.

While the first stage may be carried out at up to 100 atmospheres, this stage is preferably carried out at ambient pressure. Temperature can range from 20° to 30° C., but is preferably at about 25° C. The ratio of alkali metal cyanide to compound F is 0.1 to 0.3 moles per 100 moles, most preferably 0.25 mole.

Contacting Step A is then completed by direct addition of the acrylate derivative, preferably over a 50 to 60 minute period, at from 0° to 25° C.

For purposes of this specification, the first solvent includes, but is not limited to, such solvents as mono or di $C_{1-6}$ alkyl amide derivatives such as dimethylformamide (DMF); di-$C_{1-6}$ alkyl sulfoxide, such as methylsulfoxide or aqueous C1-6 alcohol, such as ethanol, most preferably DMF. The alkali metal cyanide is a cyanide such as sodium, potassium or lithium cyanide, preferably sodium cyanide.

The acrylate derivative, is preferably a sterically hindered acrylate, such as $CO_2$—t—$C_4C_9$. The selected acrylate is preferably added gradually over 1 hour to provide the desired γ-keto ester of formula A in a yield of approximately 80% (for R=$CO_2$—t—$C_4H_9$, 80%). Critical to reaction success was the discovery that oxygen exclusion is a requirement. In its presence, oxidative decomposition leading to by-products which depress the yield significantly;

(B) Contacting the compound of formula A in an etheral solvent with optically impure β-chlorodiisopinocampheyl borane to yield a compound of formula B

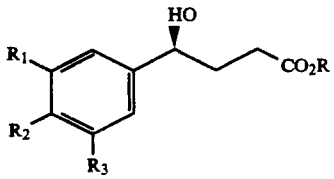

B

For purposes of this specification, etheral solvents include, but are not limited to ethers such as diethyl ether di-n-butyl and diisopentyl ethers, anisole, cyclic ethers such as tetrahydropyran, 4-methyl-1,3-dioxane, dihydropyran, tetrahydrofurfuryl methyl ether, ethyl ether, furan and 2-ethoxytetrahydrofuran, most preferably tetrahydrofuran.

The reaction can be conducted at −25° to 25° C. preferably at 0° to 5° C. The reaction is allowed to proceed until essentially complete in about 1 to 100 hours, preferably 18 hours. While the pretreatment may be carried out at up to 100 atmospheres, the reaction is preferably carried out at ambient pressure. The γ-hydroxy butanoate derivative Compound B is provided in typically 80-90% yields with an enantiomeric excess (ee) of 92%. Use of the (−)-chloroborane enantiomer provides the 4S-alcohol while the (+)-chloroborane enantiomer yields the 4R-alcohol. Thus both enantiomers of B are accessible by this invention.

In a preferred embodiment, Step B comprises:

(B₁) contacting borane methyl sulfide in ether (as defined above) with (1R)-(+)-α-pinene to yield, after acidification with an acid chloride, a composition comprising chlorodiisopinocampheyl borane,

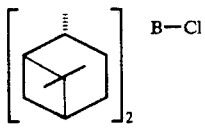

and;

(B₂) contacting, without further purification, the composition comprising chlorodiisopinocampheyl borane with a compound of Formula A

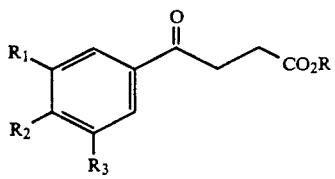

A to yield a compound of Formula B

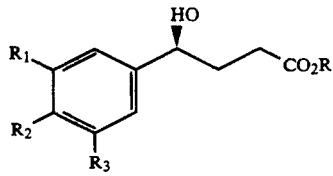

B

In this preferred class of Step B, tetrahydrofuran is once again the etheral solvent of choice. The reacton can be carried out at −25° to 25° C. Preferably, the pinene is added to the borane in THF in the absence of oxygen and in a manner calculated to maintain the temperature of the reaction mixture in a range of 0° to 5° C. This portion of the reaction is allowed to proceed until essentially complete in about 1 to 100 hours, preferably 18 hours. For purposes of this specification, acid chloride includes but is not limited to hydrochloric acid.

Typically, the compound of formula A is added at from 0° to 5° C. This portion of the reaction is allowed to proceed until for about 1 to 100 hours, preferably 74 hours, after which water, alkanol and neutralizing agent are added, preferably at under 15° C. This portion of the reaction is allowed to proceed until essentially complete in 1 to 100 hours, typically at ambient temperature for 2 hours.

The ratio of borane to pinene and acid chloride in pinene is approximately 1:2 with preferably an excess of pinene. The ratio of pinene to the butyrate (Formula A) is approximately 1:3.5; preferably with an excess of pinene.

(C) Contacting Compound B in a medium containing alcohol in an etheral solvent with an alkali metal hydroxide to yield a compound of formula C.

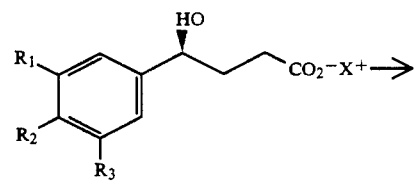

C wherein X is an alkali metal selected from the group consisting of Sodium, Potassium and Lithium.

For purposes of this specification, alcohol includes, but is not limited to $C_{1-6}$ alkanol, preferably ethanol. As before, sodium hydroxide is the preferred alkali metal hydroxide. For purposes of this specification, etheral solvents include, but are not limited to ethers such as diethyl ether di-n-butyl and diisopentyl ethers, anisole, cyclic ethers such as tetrahydropyran, 4-methyl-1,3-dioxane, dihydropyran, tetrahydrofurfuryl methyl ether, ethyl ether, furan and 2-ethoxytetrahydrofuran, most preferably tetrahydrofuran. For complete saponification, the molar ratio of alkali metal hydroxide to Compound C should be at least 1 to 1, preferably 1.5 to 1 or greater. The time, temperature and pressure of the reaction are not considered critical. The reaction can be conducted at −25° to 50° C., preferably at 25° C. The reaction is allowed to proceed until essentially complete in about 20 to 200 minutes, preferably 75 minutes. While the pretreatment may be carried out at up to 100 atmospheres, the pretreatment is preferably carried out at ambient pressure.

Highlighting this Step is the intramolecular assistance provided by the γ-hydroxyl moiety in compound B which facilitates removal of the R-oxy group under basic conditions. Normally recommended acid catalyzed procedures for hydrolysis of the R ester would likely result in significant racemization of this substrate. Saponification yields compound C as a free acid salt, readily extractable into water and consequently easily separated from the neutral pinanyl by-products resulting from the chiral reduction step.

Thereafter the acid salt of Compound C can be converted to the acid by any of the conventional means known in the art.

(D) Contacting the free acid of compound C in a second solvent with pyridinium para-toluene sulfonate to yield a compound of formula D.

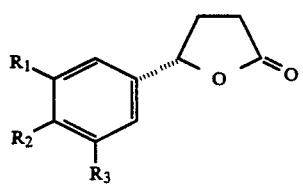

D

For purposes of this specification the second solvent includes, but is not limited to, an etheral solvent, as defined above, or a $C_{6-10}$ linear, branched or cyclic hydrocarbon solvent. Toluene is preferred. The time, temperature and pressure of the reaction are not considered critical. The reaction can be conducted at 50° to 80° C., preferably at 70° C. The reaction is allowed to proceed until essentially complete in about 20 to 200 minutes, preferably 90 minutes. While the reaction may be carried out at up to 10–100 atmospheres, the reaction is preferably carried out under ambient pressure in a nitrogen atmosphere.

Significantly, racemization does not occur, even with highly electron rich substrates.

(E) Recovering purified compound D.

The 80 to 95% optically pure product can be optically enriched to greater than 99.5% enantiomeric excess by controlled crystallization from ethyl acetate, isopropyl acetate, ethanol, methanol, or solvent mixtures of a hydrocarbon solvent such as hexanes, cyclohexane and esters such as ethyl acetate, isopropyl acetate or ethers such as methyl t-butyl ether. Preferably the optically enriched product is crystallized from an ethyl acetate/hexane mixture in a 1:6 ratio v/v at −10° C. to 20° C. This provides 99.5% ee pure Compound D.

More particularly, this invention concerns a process of making compounds of formula D wherein:
$R_1$ is iodide;
$R_2$ is selected from the group consisting of
  (a) $C_{1-12}$alkoxy,
  (b) $C_{2-6}$alkenyloxy,
  (c) substituted $C_{1-8}$alkoxy wherein the substituent is hydroxy,
  (d) $C_{1-6}$alkyl carbonyl-$C_{1-6}$alkoxy,
  (e) phenyl-$C_{1-6}$alkoxy;
$R_3$ is selected from the group consisting of
  (a) $C_{1-6}$alkoxy,
  (b) substituted $C_{1-6}$alkoxy wherein the substituent is selected from the group consisting of hydroxy,
  (c) —O—$C_{1-6}$alkyl-O—$R^{10}$, wherein $R^{10}$ is
    (1) —$PO_2(OH)^-$ $M^+$ wherein $M^+$ is a pharmaceutically acceptable cation,
    (2) —$C(O)(CH_2)_2$—$CO_2^-M^+$, or
    (3) —$SO_3^-M^+$,
  (d) $C_{1-6}$-alkylcarbonyl-$C_{1-6}$alkoxy.

As shown in Scheme 2, butyrolactone, Compound 2A, is reduced to a lactol, then silylated, providing silylactol, Compound 2B. Compound 2B is then activated through treatment with silylbromide, forming a glycosyl bromide Compound 2C. Coupling is subsequently achieved using an aryl copper species to stereoselectively produce the target trans-2,5-diaryltetrahydrofuran, Compound 2D.

SCHEME 2

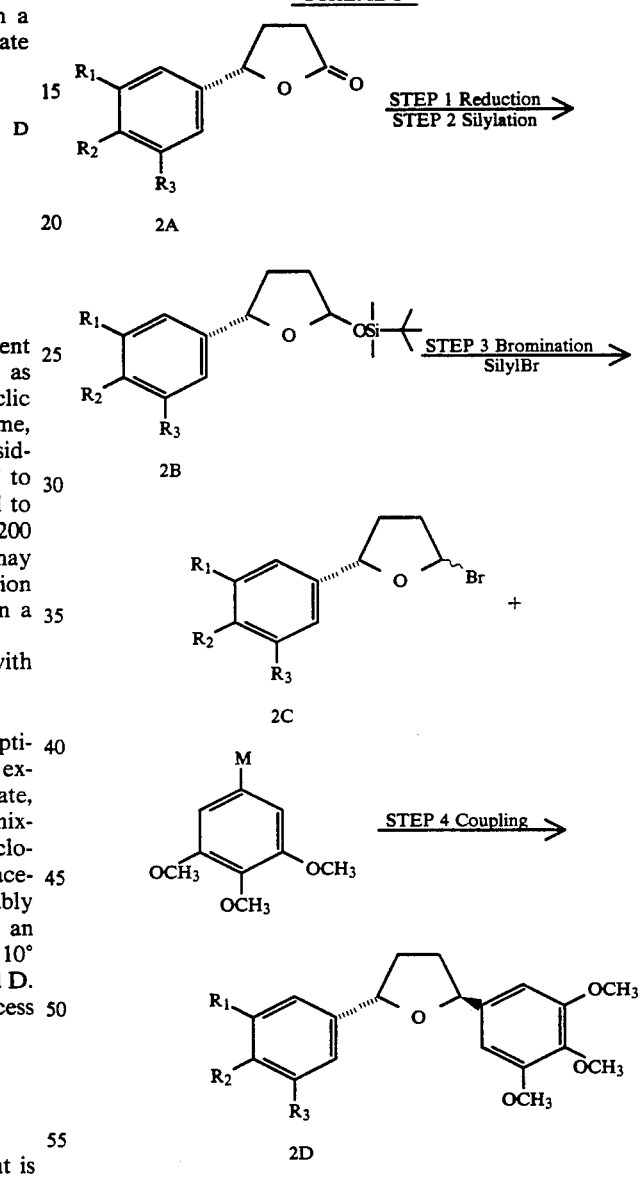

This latter process can be further elaborated in a process of making compounds of the Formula 2D,

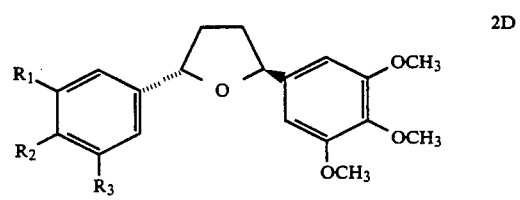

2D comprising:

(2A) contacting of a compound of the formula

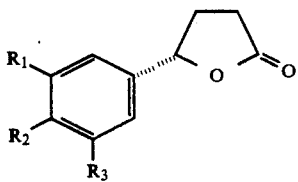

in an aromatic solvent with a reducing agent to yield Compound 2A';

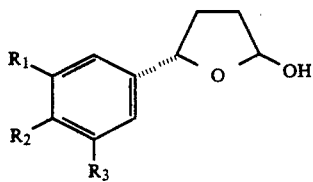

For purposes of the specification, aromatic solvents include, but are not limited to, benezene, toluene and xylene, preferably toluene. Reducing agents include, but are not limited to metal hydrides such as sodium bis-methoxy, ethoxy aluminum hydride and diisobutylaluminum hydride preferably, diisobutylaluminium hydride. For complete reaction the molar ratio of reducing agents to lactone should be approximately 1 to 1, or larger; preferably 1.25 to 1. The reaction may be conducted from $-80°$ C. to $-50°$ C., preferably $-75°$ C. to $-60°$ C. The reaction is allowed to proceed until substantially complete in about 1 to 2 hours, typically 1.25 or 1.5 hours. The reaction can then be quenched by addition of $C_{1-6}$alkanol such as methanol.

While the reaction can be carried out at up to 100 atmospheres of pressure, the reaction is preferably carried at under ambient pressure;

(2B) contacting of Compound 2A' with a tri-$C_{1-6}$alkyl chlorosilane in a second solvent and a base to yield the silyllactol Compound 2B;

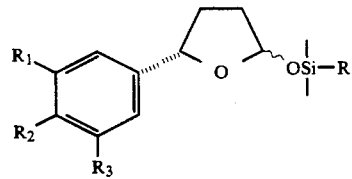

wherein R is $C_{1-6}$ alkyl.

For purposes of this specification tri-$C_{1-6}$alkylchlorosilanes include but are not limited to tri-$C_{1-6}$alkyl chlorosilane wherein each alkyl group is independently defined as $C_{1-6}$ alkyl. Preferred is tert-butyldimethylchlorosilane. The second solvent includes, but is not limited to N,N-di$C_{1-6}$alkyl carbonyl amide, such as N,N-dimethyl formamide (DMF) or toluene, tetrahydrofuron (THF), dichloromethane or other non-protic solvent; DMF is preferred. Nitrogen containing bases include but are not limited to pyrrole, pyridene, pyrrolidine tri-$C_{1-3}$alkyl amino such as triethyl amine and imidazole. Imidazole is preferred for complete reaction. The molar ratio of base to Compound A' should be approximately 2 to 1 or greater. A ratio of 2.2 to 1 is typical.

The ratio of silane to Compound 2A' is approximately 1.1 to 1 up to 2.5 to 1; preferably 1 to 1. The reaction should be allowed to proceed until complete in approximately 1 to 3 hours. The reaction temperature may be 0° to 80° C., preferably 25°-30° C.

While the reaction can be carried out at up to 100 atmospheres of pressure, the reaction is preferably carried out under ambient pressure. The presence of oxygen is preferably minimized, such as by use of a nitrogen or other inert atmosphere.

(2C) contacting of Compound 2B with a silyl bromide in a third solvent to yield a glycosyl bromide Compound 2C:

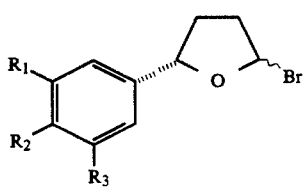

wherein the hydroxyl groups on the substituents $R_1$, $R_2$ and $R_3$ are protected.

As will be appreciated by those of skill in the art, the hydroxyl groups may be protected with groups including trialkylsilyl, acetate, benzoate, and ether. See also Protective Groups in Organic Synthesis, Theodora W. Green, John Wiley and Sons (1981).

For purposes of the specification, the third solvent includes but is not limited to etheral solvents such as diethyl ether di-n-butyl and diisopentyl ethers, anisole, cyclic ethers such as tetrahydropyran, 4-methyl-1,3-dioxane, tetrahydrofurfuryl methyl ether, ethyl ether, furan and tetrahydrofuran, or halocarbon solvents such as mono or di halo $C_{1-4}$alkyl including methylene chloride. Methylene chloride is preferred. The silyl bromide includes, but is not limited to tri $C_{1-6}$ alkylsilyl bromide with trimethylsilylbromide preferred for complete reaction. The molar ratio of silyl bromide to compound B should be 1 to 1 or greater, preferably 1.1-1.3 to 1. The reaction is allowed to proceed until essentially complete in about 0.5 to 3 hours, typically 1.5 hours.

The reaction temperature is approximately $-70°$ to $-10°$ C., preferably $-60°$ C.

While the reaction can be carried out at up to 100 atmospheres of pressure, the reaction is preferably carried at under ambient pressure. The presence of oxygen is preferably minimized, such as by use of a nitrogen or other inert atmosphere.

(2D) contacting of Compound 2C with an organo metallic reagent species of the formula

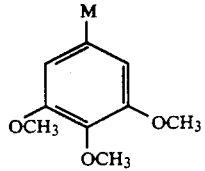

wherein M is magnesium, aluminum, zinc or copper, in a fourth solvent to yield a compound of formula 2D;

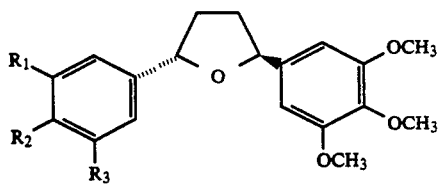

For purposes of this specification the fourth solvent includes, but is not limited to ethers as broadly defined above; preferably THF. The organo metallic reagent includes, but is not limited to those derived from aryl Grignard reagents such as 3,4,5-trimethoxy phenylmagnesium bromide in the presence of a copper salt such as copper cyanide or lithium tetrachlorocuprate.

The ratio of organometallic reagent to Compound 2C is approximately 1-1.5 to 1, preferably 1.4 to 1. The reaction is allowed to proceed until essentially complete in about 0.5 to 3 hours. Typically 1.0 hours. The reaction temperature is approximately −70° to −10° C., preferably −60° C.

While the reaction can be carried out at up to 100 atmospheres of pressure, the reaction is preferably carried at under ambient pressure. The presence of oxygen is preferably minimized, such as by use of a nitrogen or other inert atmosphere.

PAF antagonists that can be produced from the compound of Formula 2D include (−)-(2S,5S)-2-(5(2-hydroxyethylsulfonyl)-4-(n-propoxy)-3-methoxyphenyl)-5-(3,4,5-trimethoxyphenyl)tetrahydrofuran; (−)-(2S,5S)-2-(5-(2-oxopropylsulfonyl)-4-(n-propoxy)-3-(3-phosphopropoxy)phenyl-5-(3,4,5-trimethoxyphenyl)-tetrahydrofuran; (−)-(2S,5S)-2-(5-(2-oxopropylsulfonyl)-4-(n-propoxy)-3-(3-hydroxypropoxy)-phenyl-5-(3,4,5-trimethoxyphenyl)-tetrahydrofuran; and (−)-(2S,5S)-2-(5-(2-hydroxyopropylsulfonyl)-4-(n-propoxy)-3-(3-hydroxypropoxy)phenyl-5-(3,4,5-trimethoxyphenyl)-tetrahydrofuran.

The following examples illustrate the present invention and as such are not to be considered as limiting the invention set forth in the claims appended thereto.

The starting materials are either known and available.

EXAMPLE 1

4[3-methoxy-4-n-propyloxy-5-iodophenyl]-4S-Butyrolactone

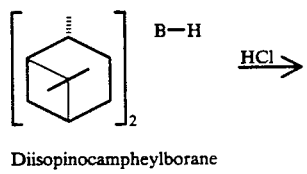

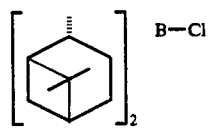

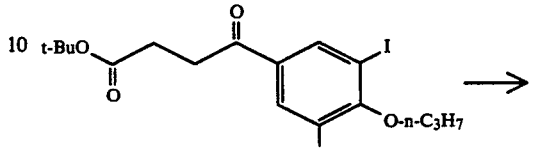

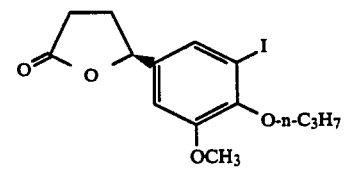

Borane methyl sulfide (2.48 mL, 0.028 mole) and 5 mL of THF are cooled to 0° C. under nitrogen. (1R)-(+)α-Pinene (91% ee) (9.79 mL, 0.062 mole) is added dropwise over 10 min maintaining the temperature at ≦5° C. A white precipitate forms in 1 h at 0° C. After stirring for 2 h, the resulting slurry is aged for 18 h at 0°-5° C. A 9.0M solution of HCl in THF (3.1 mL. 0.028 mole) is added dropwise over 15 min. Hydrogen gas is evolved during the addition. The clear solution of chloroborane is aged an additional 15 min. and tert.-butyl-4[3-methoxy-4-n-propyloxy-5-iodophenyl]-4-oxobutyrate. (7.29 g, 0.016 mole) dissolved in THF (5 mL) is added dropwise over 10 min. After 24 h at 0° C., water (6.6 mL), methanol (20 mL) and 5M NaOH (23 mL) are successively added, maintaining the temperature at <15° C. The solution is warmed to ambient temperature and aged for 2 h. The orange solution is poured into methyl t-butyl ether (MTBE) (125 ml) and saturated sodium bicarbonate (50 mL). The aqueous layer is extracted in MTBE (90 mL). The alkaline layer is acidified to pH 2 with 2N HCl, and extracted with toluene. (2×100 mL).

Pyridinium p-toluenesulfonate (40 mg) is added to the combined toluene extracts and the solution is heated to 70° C. under vacuum for 1 h. The solution is cooled to ambient temperature and washed with saturated sodium bicarbonate (100 mL) and 5% aqueous sodium chloride (100 mL). The solvent is removed in vacuo providing the title lactone as a solid. The ee as determined by $^1$H NMR (300 MHz) using (S)-(+)-2,2,2-trifluoro-1-(9-anthryl)ethanol is 88%.

EXAMPLE 2

Lactone Recrystallization

In cases in which the initially isolated lactone is not suitable for continued processing [<99.5% ee]. The following recrystallization procedure is employed.

| Materials | |
|---|---|
| 4[3-Methoxy-4-n-propyloxy-5-iodophenyl]-4S-butyrolactone | 1.656 kg |
| Ethyl acetate | 1.9 L |
| Hexanes | 7.2 L |

Crude lactone [1.656 kg] is dissolved in ethyl acetate (1.65 L) at 45° C. and filtered from insolubles [ca. 5 g]. The insolubles are washed with 250 ml of ethyl acetate. Hexanes (1.8 L) are added to the combined filterate plus washes and seeded with 100 mg of lactone. Additional hexanes (5.46 L) are added and the batch allowed to crystallize for one half hour at 25° C. Crystallization is completed by aging overnight in the cold room. The solids are filtered, washed with 3×500 ml of cold hexanes/ethyl acetate [4/1] and dried in vacuo at 25° C. to yield 1.377 kg [83.2%].

NMR [4 mg lactone+40 mg (S)-(+)-2,2,2-trifluoro-1(9-anthryl)ethanol in CD$_2$Cl$_2$] showed >99.5% ee; HPLC (wt. %) was 98.9%

EXAMPLE 3

Step A: 4[3-Methoxy-4-n-propyloxy-5-(2'-t-butyldimethylsiloxyethylsulfonyl)phenyl]-4-butyrolactol

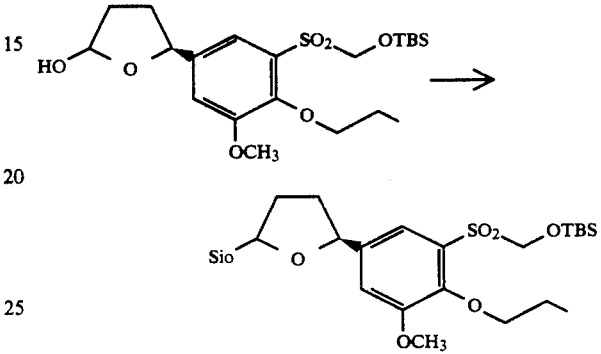

C$_{22}$H$_{36}$O$_7$SiS
MW 472

C$_{22}$H$_{38}$O$_7$SiS
MW 474

| Materials | Amt | Mols | MW |
|---|---|---|---|
| 4[3-Methoxy-4-n-propyloxy-5-(2'-t-butyldimethylsiloxyethylsulfonyl)phenyl]-4-butyrolactone | 1.607 Kg | 3.405 | 472 |
| Diisobutylaluminum hydride 1.5 M in toluene | 3.5 L | 5.25 | 1.5 M |
| Methanol (d = 0.791) | 1.5 L | 37.08 | 32 |
| Potassium sodium tartrate tetrahydrate | 12 L | | 281.2 |
| Ethyl Acetate | 12 L | | |
| Toluene | 13 L | | |

To a solution of the lactone (1.607 kg, 3.405 mole) in sieve dried toluene (13 L) at −72° C. is added a 1.5M toluene solution of diisobutylaluminum hydride (3.50 L, 5.25 mole) dropwise over 1.25 hours maintaining an internal temperature of <−65° C. The mixture is stirred at −70° C. for 1.0 hour.

The reaction is quenched through the slow addition of methanol (1.5 L) at −70° C. then the mixture is warmed to −20° C. Saturated Rochelles's salt (12 L) is added over 0.5 hours keeping the temperature <10° C. and the mixture then stirred at 5° C. for 1.5 hours, then the two phases separated. The aqueous layer is extracted with ethyl acetate (12 L). The organic phase is washed with DI water (2×8.0 L) and with saturated aqueous sodium chloride (10 L). The organic extracts are concentrated in vacuo. The resulting yellow oil is flushed twice with toluene (2×1 L) to provide 1.799 Kg of the lactol as a light yellow oil.

HPLC assay indicated this product to be 87 wt % pure (97% yield). The lactol is suitable for use without further purification.

Step B: 5[3-Methoxy-4-n-propyloxy-5-(2'-t-butyldimethylsiloxyethylsulfonyl)phenyl]-1-(t-butyldimethylsiloxy)-butyrolactol

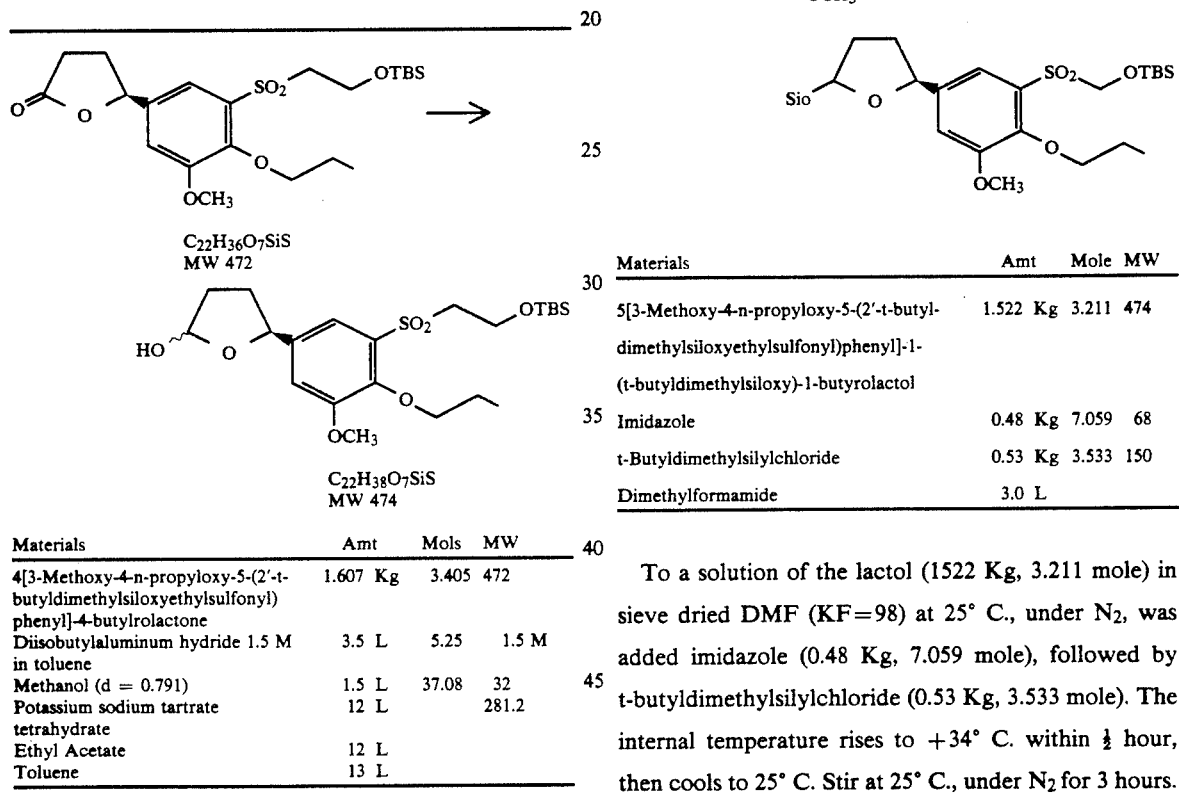

| Materials | Amt | Mole | MW |
|---|---|---|---|
| 5[3-Methoxy-4-n-propyloxy-5-(2'-t-butyldimethylsiloxyethylsulfonyl)phenyl]-1-(t-butyldimethylsiloxy)-1-butyrolactol | 1.522 Kg | 3.211 | 474 |
| Imidazole | 0.48 Kg | 7.059 | 68 |
| t-Butyldimethylsilylchloride | 0.53 Kg | 3.533 | 150 |
| Dimethylformamide | 3.0 L | | |

To a solution of the lactol (1522 Kg, 3.211 mole) in sieve dried DMF (KF=98) at 25° C., under N$_2$, was added imidazole (0.48 Kg, 7.059 mole), followed by t-butyldimethylsilylchloride (0.53 Kg, 3.533 mole). The internal temperature rises to +34° C. within ½ hour, then cools to 25° C. Stir at 25° C., under N$_2$ for 3 hours. The reaction was diluted with EtOAc (20 liter), washed with H$_2$O (3×10 L) followed by a 10:1 mixture of saturated Brine/H$_2$O (10 L). The organics were concentrated to afford 2.170 Kg of a yellow oil. 300 MHz NMR is consistent for silyl hemiacetal.

HPLC assay indicated this product to be 87.5% pure (100% yield). This material is suitable for use without further purification.

Step C: Preparation of 1-tert-butyldimethylsiloxy-2-((2-methoxy-2-propyloxy-5-(tetrahydro-5-(3,4,5-trimethoxyphenyl)-2-furanyl)phenylsulfonyl-trans-(−)-ethane

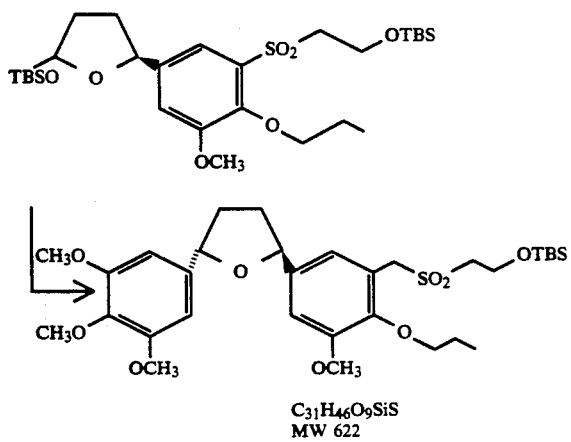

C₃₁H₄₆O₉SiS
MW 622

| Materials | | |
|---|---|---|
| Silyl ether | 0.829 Kg | 1.409 mole |
| TMS-Br | 0.232 L | 1.759 mole |
| Li₂CuCl₄/THF 0.5 M | 0.060 L | 0.030 mole |
| 3,4,5-trimethoxyphenyl magnesium bromide (0.9 M in THF) | 2.25 L | 2.025 mole |
| CH₂Cl₂ | 6.0 L | |
| Ethyl Acetate | 13 L | |

In a 50 L flask, the silyl ether B (0.829 Kg, 1.409 mole) was dissolved in CH₂Cl₂, under N₂. The mixture was cooled to −60° C. and then neat trimethylsilylbromide (0.232 L, 1.759 mole) was added. The mixture was stirred at −60° C. for 1.5 hours. In a separate flask containing 3,4,5-trimethoxyphenylmagnesium bromide (0.9M, 2.5 L, 2.025 mole), at 0° C. under N₂ was added the THF solution of Li₂CuCl₄ (0.060 mL, 0.030 mole).

To the glycosyl bromide at −60° C. was transferred the solution of organometallic. After complete addition, the reaction was stirred at −60° C. for 1.0 hours. It was quenched at −60° C. by addition of 10 L of saturated NH₄Cl/NH₄OH (10:1 v/v), and H₂O (5 L). Allow to stir without external cooling for 0.5 hours. After separating the organic layer, the aqueous layer was extracted with EtOAc (10 L) and the combined organics were washed with brine (8 L). The resulting clear, homogeneous organic layer was concentrated to afford 1.178 Kg of a red oil. Analysis of the crude reaction mixture by HPLC assay showed 0.754 Kg (86%) of the title compound.

PREPARATION OF STARTING MATERIALS
EXAMPLE A
4-[3-Methoxy-4-n-propyl-5-(2'-hydroxyethylthio)-phenyl]-4-butyrolactone

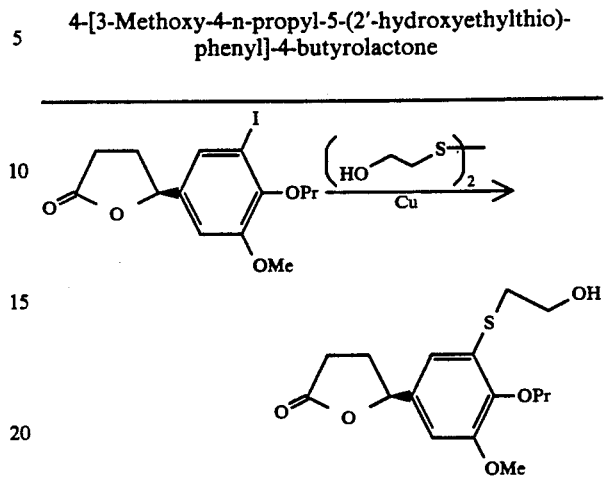

| Materials | Amount | Moles | MW |
|---|---|---|---|
| 4-[3-Methoxy-4-n-propyl-5-idophenyl]-4-butyrolactone | 2.0 g | 5.33 mmol | 376.0 |
| Copper Powder (99% for organic synthesis - Aldrich) | 0.51 g | 7.99 mmol | 63.5 |
| 2-Hydroxyethyl disulfide (Aldrich 95%) | 0.66 g | 4.26 mmol | 154.2 |
| Dimethylformamide | 15 ml | | |
| Ethyl acetate | 65 ml | | |

Iodolactone (2.0 g, 5.33 mmol) is dissolved in dimethylformamide (15 ml KF<200 μg/ml) at ambient temperature. Copper powder (0.51 g, 7.995 mmol) and then 2-hydroxyethyl disulfide (0.66 g, 4.264 mmol) is added to the solution. The mixture is heated to 108° C. for 22 hours. HPLC analysis [C-8, acetonitrile:water:phosphoric acid 60:40:0.1, 254 nm] shows no starting iodide and 3-5% formate ester byproduct.

| Iodolactone: | retention times = 8.8 min. |
|---|---|
| Formate ester: | retention times = 5.0 min. |
| Sulfide: | retention times = 3.2 min. |

The mixture is cooled to ambient temperature and 40 mL of ethyl acetate is added. The solution is stirred for 15 minutes and filtered through a celite pad. The addition of ethyl acetate prior to filtration greatly improves phase separation. The cake is washed with 25 ml of ethyl acetate. The combined organic extracts are washed with 3×40 ml of an ammonium chloride:ammonium hydroxide solution, followed by 40 ml of water. The ammonium chloride:ammonium hydroxide solution is prepared by adding approximately 65 ml of ammonium hydroxide solution (30%) to 300 ml of saturated aqueous ammonium chloride to a pH of 9.0. A pH range of 8.5-10.0 for this work has been determined to be satisfactory although pH 9.0 is favorable.

The organic extract is concentrated in vacuo to a volume of 4 ml. The solution is flushed with 2×20 ml of acetonitrile and concentrated to ~4 mL. The acetonitrile solution is used directly for the next step.

HPLC assay typically shows an 85-90% yield. ¹H-NMR (300 MHz, CDCl₃) δ 6.89 (d, J=1.8 Hz, 1H), 6.76 (d, J=1.8 Hz, 1H), 5.40 (dd, J=6.0, 8.2 Hz, 1H), 3.95 (t, J=6.8 Hz, 2H), 3.83 (s, 3H), 3.66 (q, J=6.0 Hz, 2H), 3.04 (t, J=5.9 Hz, 2H), 2.69-2.59 (m, 4H), 2.20-2.13 (m, 1H), 1.81 (sextet, J=7.1 Hz, 2H), 1.03 (t, J=7.4 Hz, 3H).

$^{13}$C-NMR (300 MHz, CDCl$_3$) δ 176.8, 153.3, 147.5, 135.5, 129.8, 119.6, 108.4, 80.9, 75.2, 60.3, 56.1, 36.5, 31.0, 29.1, 23.5, 10.5

EXAMPLE B

4-[3-Methoxy-4-n-propyl-5-(2'-hydroxyethylsulfonyl)-phenyl]-4-butyrolactone

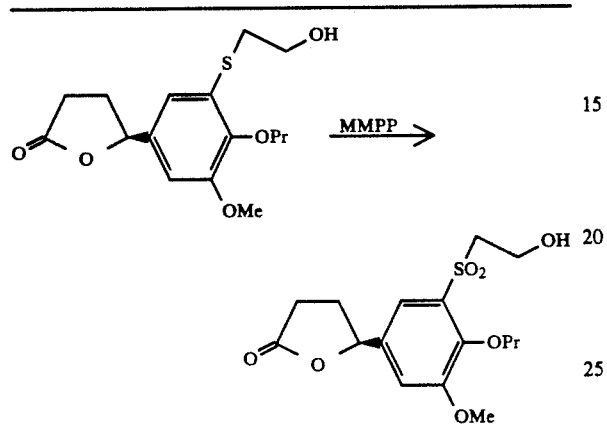

| Materials | Amount | Moles | MW |
| --- | --- | --- | --- |
| 4-[3-Methoxy-4-n-propyl-5-(2'-hydroxyethylsulfonyl)phenyl]-4-butyrolactone | 5.00 g | 15.3 mmol | 326.0 |
| Monoperoxyphthalic acid magnesium salt | 13.66 g | 27.6 mmol | 494.6 |
| Acetonitrile | 27 ml | | |
| Water | 40 ml | | |
| Saturated NaHCO$_3$ | 195 ml | | |
| 5% NaCl | 50 ml | | |
| Ethyl Acetate | 110 ml | | |
| DMF | 100 ml | | |

Monoperoxyphthalic acid magnesium salt (13.66 g, 27.6 mmol) was suspended in 40 ml of water at ambient temperature. A solution of sulfide (5.0 g, 15.3 mmol) in 27 ml of acetonitrile was added dropwise over 15 minutes keeping the temperature at <30° C. The mixture was then heated to 50° C. for 2 hours. HPLC analysis [C-8 acetonitrile:water:phosphoric acid 30:70:0.1, 10 minute gradient to 80:20:0.1, 254 nm] shows no sulfide or sulfoxide remaining.

Sulfide RT=9.9 min.
Sulfoxide RT=5.5 min.
Sulfone RT=7.7 min.

After cooling to room temperature, 65 mL of saturated sodium bicarbonate was added over 5 minutes (gas evolution and the mixture was extracted with 55 ml of ethyl acetate. The aqueous layer was back extracted with 55 ml of ethyl acetate and the combined organics were washed with saturated sodium bicarbonate (2×65 ml) and 5% aqueous sodium chloride (50 mL). The organic extracts were concentrated in vacuo to a volume of 20 ml. DMF (100 ml) was added and then concentrated in vacuo to 20 ml. The solution is used for the next step. HPLC typically shows 95% yield.

$^1$H-NMR (300 MHz, CDCl$_3$) δ 7.43 (d, J=1.8 Hz, 1H), 7.20 (d, J=1.9 Hz, 1H), 550 (dd, J=6.0, 8.7 Hz, 1H), 4.12 (m, 2H), 3.96 (t, J=5.2 Hz, 2H), 3.92 (s, 3H), 3.67–3.63 (m, 2H), 2.79–2.66 (m, 4H), 2.23–2.10 (m, 1H), 1.86 (sextet, J=7.2 Hz, 2H), 1.03 (t, J=7.4 Hz, 3H).

$^{13}$C-NMR (300 MHz, CDCl$_3$) δ 176.3, 154.1, 146.8, 135.6, 133.1, 117.4, 114.7, 80.2, 76.5, 57.5, 56.5, 30.9, 29.1, 23.2, 10.3.

EXAMPLE C

4-[3-Methoxy-4-n-propyloxy-5-(2'-t-butyl-dimethyl-siloxyethylsulfonyl)phenyl]-4-butyrolactone

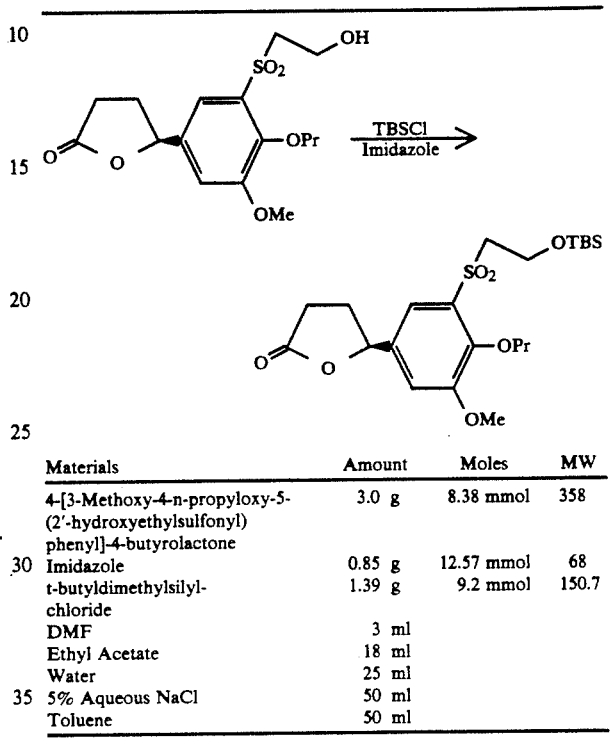

| Materials | Amount | Moles | MW |
| --- | --- | --- | --- |
| 4-[3-Methoxy-4-n-propyloxy-5-(2'-hydroxyethylsulfonyl)phenyl]-4-butyrolactone | 3.0 g | 8.38 mmol | 358 |
| Imidazole | 0.85 g | 12.57 mmol | 68 |
| t-butyldimethylsilyl-chloride | 1.39 g | 9.2 mmol | 150.7 |
| DMF | 3 ml | | |
| Ethyl Acetate | 18 ml | | |
| Water | 25 ml | | |
| 5% Aqueous NaCl | 50 ml | | |
| Toluene | 50 ml | | |

Imidazole (0.85 g, 12.57 mmol) was added to a solution of sulfone (3.0 g, 8.38 mmol) in 6 ml of DMF (KF+278 μg/ml) at room temperature (25° C.). A solution of t-butyldimethylsilylchloride (1.39 g, 9.2 mmol) in 3 ml of sieve dried DMF was added over 10 minutes keeping temperature ≦30° C. The mixture was stirred at 25° C. for 2 hours and the reaction followed by HPLC. HPLC assay [CH$_3$CN:H$_2$O:phosphoric acid 50:50:0.1 gradient to 80:20:0.1 over 8 minutes; C-8, 294 nm].

Alcohol RT=3.0 min.
Silyl ether RT=14.1 min.

Ethyl acetate (38 ml) was added and the mixture was washed with 25 ml water and then 2×25 ml with 5% aqueous sodium chloride. The organic extracts were concentrated in vacuo to a volume of 10 ml. Toluene (50 ml) was added and the solution was concentrated to a volume of 10 ml and checked by NMR for ethyl acetate (typically <5% EtOAc). HPLC assay typically shows 95% yield.

$^1$H-NMR (300 MHz, CDCl$_3$) δ 7.38 (d, J=1.9 Hz, 1H), 7.15 (d, J=1.9 Hz, 1H), 5.46 (dd, J=5.8, 8.6 Hz, 1H), 4.10 (m, 2H), 3.95 (t, J=6.1 Hz, 2H), 3.89 (s, 3H), 3.72–3.57 (m, 2H), 2.67–2.61 (m, 3H), 2.20–2.10 (m, 1H), 1.86 (sextet, J=7.2 Hz, 3H), 1.03 (t, J=7.4 Hz, 3H), 0.73 (s, 9H), −0.092 (s, 3H), −0.097 (s, 3H).

$^{13}$C-NMR (300 MHz, CDCl$_3$) δ 176.4, 154.0, 146.9, 135.1, 134.5, 117.2, 114.3, 80.4, 76.1, 57.6, 57.1, 56.4, 30.9, 29.1, 25.6, 23.2, 18.0, 10.3, −5.7.

What is claimed is:

1. A process of making diisopinocampheylchloroborane comprising:
   (a) contacting borane methylsulfide in an etheral solvent with (1R)-(+)-α-pinene, having optical purity of between about 91% ee to 95% ee, to form the diisopinocampheylborane of Formula I,

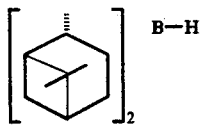

(b) contacting, without further purification, the impure product of step (a) with an acidic chloride to yield diisopinocamphenylchloroborane of Formula 2;

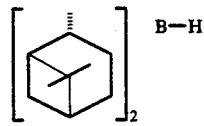

2. A process according to claim 1 conducted at from −25° to 25° C., until substaintially complete.

3. A process according to claim 2 wherein the etheral solvent is tetrahydrofuran.

4. A process for reducing a prochiral ketone to produce an optically active alcohol of high optical purity comprising reacting a prochiral ketone with a diisopinocampheylchloroborane reducing composition said composition being the product of claim 1, said reaction proceeding for from 7 hours to 24 days at a temperature of from −25° C. to ambient temperature and at ambient pressure until the reaction is complete.

* * * * *